(12) United States Patent
Collins

(10) Patent No.: US 6,358,683 B1
(45) Date of Patent: *Mar. 19, 2002

(54) BLOOD-BASED ASSAYS FOR BREAST CANCER

(75) Inventor: Colin Collins, San Rafael, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/324,393

(22) Filed: Jun. 3, 1999

(51) Int. Cl.[7] ............................................. C12Q 1/68
(52) U.S. Cl. ............................. 435/6; 435/4; 435/7.92; 435/15; 435/194
(58) Field of Search .......................... 435/6, 7.92, 194, 435/15, 4

(56) References Cited

U.S. PATENT DOCUMENTS 5,801,021 A   9/1998   Gray et al.

OTHER PUBLICATIONS

Scarpa et al. Molecular approach in human tumor investigation: oncogenes, tumor suppressor genes and DNA tumor polyomaviruses (review). Int J Mol Med. Jun. 1998, vol. 1, pp. 1011–1023.*

Tani et al. Human M2–type pyruvate kinase mRNA. Accession No. M23725. Apr. 27, 1993.*

Eigenbrodt et al. Quantification of tumor type M2 pyruvate kinase (Tu M2–PK) in human carcinomas. Anticancer Res. Jul.–Aug. 1997, vol. 17, pp. 3153–3156.*

Hennipman et al. Glycolytic enzymes in breast cancer, benign breast disease and normal breast tissue. Tumour Biol. 1987, vol. 8, pp. 251–263.*

Melnikow J et al. Cancer prevention and screening in women. Prim Care. Mar. 1997, vol. 24, pp. 15–26.*

Evans et al. Correlations between the mammographic features of ductal carcinoma in situ (DCIS) and C–erbB–2 oncogene expression. Nottingham Breast Team. Clin Radiol. Aug. 1994, vol. 49, pp. 559–562.*

Collins, C. et al., (1998) Positional Cloning of ZNF217 and NABC1: Genes Amplified at 20q13.2 and Overexpressed in Breast Carcinoma. Proceedings of the National Academy of Sciences of the United States of America 95:8703–8.

Courjal, F. et al., (1996) DNA Amplifications at 20q13 and MDM2 Define Distinct Subsets of Evolved Breast and Ovarian Tumours British Journal of Cancer 74:1984–1989.

Eigenbrodt, E. et al., (1992) Double role for Pyruvate Kinase Type M2 in the Expansion of Phosphometabolite Pools Found in Tumor Cells. Critical Reviews in Oncogenesis 3:91–115.

Hacker, H.J. et al., (1998) Pyruvate Kinase Isoenzyme Shift From L–Type to M2–type is a Late Event in Hepatocarcinogenesis Induced in Rats by a Choline–Deficient/DL–Ethionine–Supplemented Diet. Carcinogenesis 19:99–107.

Tanner, M.M. et al., (1994) Increased Copy Number at 20q13 in Breast Cancer: Defining the Critical Region and Exclusion of Candidate Genes. Cancer Research 54:4257–60.

Tanner, M.M. et al. (1995) Amplification of Chromosomal Region 20q13 in Invasive Breast Cancer: Prognostic Implications. Clinical Cancer Research 1:1455–1461.

Zwerschke, W. et al., (1999) Modulation of Type M2 Pyruvate Kinase Activity by the Human Papillomavirus Type 16 E7 Oncoprotein. Proceedings of the National Academy of Sciences of the United States of America 96:1291–6.

* cited by examiner

Primary Examiner—Nashaat T. Nashed
Assistant Examiner—Christian L. Fronda
(74) Attorney, Agent, or Firm—Townsend & Townsend & Crew LLP

(57) ABSTRACT

The present invention provides methods for detecting a breast cancer based on detecting the level of any of a number of markers, wherein the level of the marker reflects the presence of breast cancer cells in a patient. This invention is based upon the surprising discovery that certain proteins that have not been previously associated with breast cancer are in fact elevated in tissues of patients with breast cancer, and thus provide methods for diagnosis of breast cancer.

7 Claims, No Drawings

BLOOD-BASED ASSAYS FOR BREAST CANCER

BACKGROUND OF THE INVENTION

Excluding cancers of the skin, breast cancer is the most common cancer among women, accounting for one out of every three cancer diagnoses in the United States. In 1997, approximately 180,200 new cases of invasive breast cancer are expected to be diagnosed, and 43,900 women are expected to die from this disease. Only lung cancer causes more cancer deaths in women.

Currently, the primary method of detecting breast cancer in women is through mammography, or by physical examination. Unlike numerous other cancers, at present no method is available to reliably detect the existence of breast cancer by examining the level of specific blood markers. For example, in the case of prostate cancer, the antigen PSA (for prostate specific antigen) can be detected in the blood and is indicative of the presence of prostate cancer. Thus, the blood of men at risk for prostate cancer can be quickly, easily, and safely screened for elevated PSA levels. No such method currently exists for women at risk of breast cancer. This invention addresses this and other needs.

SUMMARY OF THE INVENTION

The present invention provides methods of detecting markers from a biological sample from a patient, wherein the level of the marker indicates the presence of breast cancer in the patient.

In numerous embodiments of the invention, a method for assessing the presence of a breast cancer in a patient will include several steps, including providing a biological sample from the patient, detecting the level of one or more markers in the sample, and comparing the level of the one or more markers with a control level that is representative of a level in a normal, cancer-free patient. Using such methods, an elevation of marker level in a patient compared to the control level indicates the presence of breast cancer in the patient.

In preferred embodiments, the marker used in this invention will be M2 Pyruvate Kinase, or a derivative or fragment thereof. Also preferred is the use of hnRNPK, or derivatives or fragments thereof. The invention also provides methods for identifying novel molecules useful in the assays described herein.

In preferred embodiments, the level of a marker will be measured in a blood sample. The "level" as used herein can refer to MRNA level, DNA level, protein level, enzyme activity, the presence of particular isoforms, or any other marker of gene number, expression, or activity. In particularly preferred embodiments, the protein level of one or more marker described herein will be measured.

In preferred embodiments, the level of marker will be quantitated and compared with a control value or sample. In particularly preferred embodiments, the difference between an elevated level and a control level will be statistically significant.

In numerous embodiments, the present methods will further include an additional step, wherein an additional diagnostic step specific to breast cancer will be performed. For example, following a detection of an elevated level of a marker, which elevated level indicates the presence of a breast cancer, the indication will be confirmed using one or more techniques specific to breast cancer detection, such as mammography, physical examination, biopsy, etc.

Definitions

A "blood sample" refers to an amount of blood removed to allow diagnostic analysis of components within the blood. These components may be blood cells, such as lymphocytes or other white blood cells, or may be blood fractions that are partially or completely devoid of cells, e.g., plasma or serum). A blood sample can also refer to cells removed from bone marrow.

When a cell is said to have an "elevated level" of a marker, it means that it has a level of the marker that is measurably or detectably higher than the level of the marker in a normal, non-cancerous cell. The difference between the higher level of the marker and the normal level may be based on quantitative or qualitative methods of detection.

The phrase "detecting a breast cancer" refers to the ascertainment of the presence or absence of breast cancer in an animal. "Detecting a breast cancer" can also refer to obtaining indirect evidence regarding the likelihood of the presence of cancerous cells in the animal. Detecting a breast cancer can be accomplished using the methods of this invention alone, or in combination with other methods or in light of other information regarding the state of health of the animal.

A "breast cancer" in an animal refers to the presence of cells originating in the breast that possess characteristics typical of cancer-causing cells, such as uncontrolled proliferation, immortality, metastatic potential, rapid growth and proliferation rate, and certain characteristic morphological features. Often, breast cancer cells will be in the form of a tumor, but such cells may also exist alone within a patient.

"Providing a biological sample" means to obtain a biological sample for use in the methods described in this invention. Most often, this will be done by removing a sample of cells from a patient, but can also be accomplished by using previously isolated cells (e.g., isolated by another person), or by performing the methods of the invention in vivo.

A "biological sample" refers to a cell or population of cells or a quantity of tissue or fluid from a human. Most often, the sample has been removed from a human, but the term "biological sample" can also refer to cells or tissue analyzed in vivo, i.e. without removal from a human. Often, a "biological sample" will contain cells from the human, but the term can also refer to non-cellular biological material, such as non-cellular fractions of blood, saliva, or urine, that can be used to measure marker levels.

"Tissue biopsy" refers to the removal of a biological sample for diagnostic analysis. In a patient with cancer, tissue may be removed from a tumor, allowing the analysis of cells within the tumor.

"Detecting a level of a marker" refers to determining the expression level of a gene or genes encoding a target polypeptide. The copy number of a gene can be measured in multiple ways known to those of skill in the art, including, but not limited to, Comparative Genomic Hybridization (CGH) and quantitative DNA amplification (e.g., quantitative PCR). Gene expression can be monitored in a variety of ways, including by detecting mRNA levels, protein levels, or protein activity, any of which can be measured using standard techniques. Detection can involve quantification of the level of (e.g., gDNA, cDNA, MRNA, protein, or enzyme activity), or, alternatively, can be a qualitative assessment of the level of a target, in particular in comparison with a control level.

To "compare" levels of markers means to detect marker levels in two samples and to determine whether the levels are equal or if one or the other is greater. A comparison can be done between quantified levels, allowing statistical comparison between the two values, or in the absence of quantification, for example using qualitative methods of detection such as visual assessment by a human.

A "control sample" refers to a sample of biological material representative of healthy, cancer-free humans. The level of a target in a control sample is desirably typical of the general population of normal, cancer-free humans. This sample can be removed from a patient expressly for use in the methods described in this invention, or can be any biological material representative of normal, cancer-free humans, including cancer-free biological material taken from a human with cancer elsewhere in its body. A control sample can also refer to an established level of a target, representative of the cancer-free population, that has been previously established based on measurements from normal, cancer-free humans.

An "increased level of a target" means a level of a target polypeptide (e.g. M2PK), that, in comparison with a control level of the target polypeptide, is detectably higher. The method of comparison can be statistical, using quantified values for the level of the target, or can be compared using non-statistical means, such as by visual assessment by a human.

When a level of a target (e.g., M2PK) mRNA, protein, enzyme activity, or copy number is "measured," it is assessed using qualitative or quantitative methods. Preferably, the level is determined using quantitative means, allowing the statistical comparison of values obtained from biological samples and control values. The level can also be determined using qualitative methods, such as the visual analysis and comparison by a human of multiple visibly labeled samples, e.g., fluorescently labeled samples detected using a fluorescent microscope or other optical detector (e.g., image analysis system, etc.).

DESCRIPTION OF THE SPECIFIC EMBODIMENTS

The present invention provides methods for detecting a breast cancer based on detecting the level of any of a number of markers, wherein the level of the marker reflects the presence of breast cancer cells in a patient. This invention is based upon the surprising discovery that certain proteins that have not been previously associated with breast cancer are in fact elevated in tissues of patients with breast cancer, and thus provide methods for diagnosis of breast cancer.

It has previously been identified that the ZNF2 17 gene is elevated in breast cancer cells (see, e.g., WO 98/02537, the gene is referred to as ZABC1 in this document). It has now been discovered that a number of proteins bind to the ZNF217 gene product, and which are themselves elevated in breast cancer cells. These ZNF217-binding proteins are thus markers for breast cancer cells, and can be used for the diagnosis of breast cancer in a patient, alone or in combination with other diagnostic methods.

In particular, two proteins, M2 Pyruvate Kinase (M2PK), and heterogeneous nuclear ribonucleoprotein K (hnRNPK) were found to bind to ZNF217 protein and to be highly expressed in breast cancer cells. The present invention provides methods for diagnosing breast cancer through the detection of the level of the genes encoding these proteins, or through the detection of the level of gene product itself. This invention also provides methods for identifying additional proteins that can be used in the diagnosis of breast cancer.

I. Markers

Any of a number of markers can be used to detect breast cancer according to the present methods. In preferred embodiments, the level of M2 Pyruvate Kinase (M2PK), or any derivative, variation, or fragment thereof, or of Heterogeneous Nuclear Ribonucleoprotein K (hnRNPK) can be used.

M2PK (see, e.g., GenBank accession numbers P14786, S30038, A33983) is a glycolytic enzyme that can exist as a tetramer with high affinity for its substrate, phosphoenolpyruvate, or as dimer with low substrate affinity (Eigenbrodt et al., 1997). In tumors the low activity dimeric isoenzyme predominates. The metabolic consequences of this M2PK inactivation include increased aerobic glycolysis, increased biosynthetic capability and decreased requirement for oxygen. Stabilization of M2PK in the inactive form has been associated with HPV16 E7 protein binding to it (Zwerschke et al., 1999). Binding of M2PK by ZNF217 suggests that ZNF217 may mimic E7 and induce a metabolic state permissive for cell proliferation in breast cancer cells.

hnRNPK (see, e.g., Q07244 or NP_002131) is a transcription factor that can modulate expression of genes such as CMYC and thymidine kinase (TK) (Michelotti et al., 1996; Hsieh et al., 1998). The observation that ZNF217 binds hnRNPK indicates that these proteins may collaborate to regulate expression of important growth and immortalization related genes.

In numerous embodiments, the level of M2PK, hnRNPK, or other proteins will be assessed. For example, the level of M2PK mRNA, gene copy number, protein level, or enzyme activity will be assessed using standard techniques. As explained below, preferred means of detecting, e.g., increased M2PK levels is the analysis of protein levels in blood using immunoassays such as ELISA assays, as described below (see, e.g., Eigenbrodt et al. (1997) *Anticancer Res.* 17:3153–5156.

In addition, any other ZNF217 binding protein, such as splicing factor Srp30c, cDNAs with homology to RNA binding proteins, and laminin binding protein (LBP) can be used. Additional ZNF217-associating molecules can easily be identified using standard techniques, e.g., 2-hybrid screens, GST pull-down, co-immunoprecipitations, affinity chromatography, etc. Preferably, the level of any molecules, e.g., genes or proteins, identified using such methods will be assayed in breast cancer cells, wherein a molecule found to associate with ZNF217 and to be expressed at high levels in breast cancer cells can be effectively used in the present methods.

In addition, the ZNF217 protein can be used (see, e.g., WO 98/02539, wherein the gene is referred to as ZABC1) to detect the presence of a breast cancer. In preferred embodiments, the level of ZNF217 is detected in the blood using an immunoassay, e.g., ELISA.

In numerous embodiments, the level of more than one marker will be detected in a single biological sample. Such combinations of marker detection can be used, e.g., to confirm or refine the diagnostic indication provided by a single marker level alone. For example, the M2PK level, which can reflect the presence of any of several types of cancer, e.g., colon cancer, breast cancer, etc., can be detected simultaneously to or prior to the detection of the ZNF217 level, wherein an elevated level of M2PK and ZNF217 indicates the presence of one type of cancer alone, e.g., breast cancer.

The manipulation of any of the marker genes or proteins described herein, e.g., for the purpose of producing protein or nucleic acids, or for creating variants, derivatives, fragments, etc., of any of the markers, can be accomplished using standard molecular biological techniques, as described, e.g., in Ausubel et al. (ed.) (1990) Current Protocols in Molecular biology, Greene Publishing and Wiley-Interscience, New York, Glover (ed.) (1987) *DNA Cloning: A Practical Approach*, vols 1–3, IRL Press, Oxford, or Sambrook et al. (1989) Molecular Cloning: A Laboratory Manual, 2d Ed., vols 1–3, Cold Spring Harbor Press, New York.

II. Treating breast cancer

The markers described herein can also be used to reduce the growth and/or proliferation of breast cancer cells. Such inhibition can be an effective treatment, alone or in combination with other treatments, for breast cancer. For example, ZNF217 and/or M2PK, each of which is present at abnormally high levels in breast cancer cells, can be inhibited using any of a large number of standard techniques, such as antisense, ribozymes, dominant negatives, small molecule inhibitors, antibodies, and others. The selection, isolation, synthesis, and use of such inhibitory techniques is well known to those of skill in the art.

III. Assays of marker levels

As indicated above, assays of the copy number or level of activity or expression of any of the proteins described herein provide a measure of the presence or likelihood of a breast cancer. The sequence of these proteins are known and hence, copy number can be directly measured according to a number of different methods as described below.

A. Detection of Copy Number

In one embodiment, the presence of, or predilection to cancer, is evaluated simply by a determination of the copy number of a marker gene. Methods of evaluating the copy number of a particular gene are well known to those of skill in the art. For example, the genomic location of the M2PK gene, 15q22, is amplified in certain cancer cells and can be detected using the methods provided herein.

1. Hybridization-based Assays

One method for evaluating the copy number of marker-encoding nucleic acid in a sample involves a Southern transfer. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid.

An alternative means for determining the copy number of any of the marker genes described herein is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate(e.g. membrane or glass) bound methods or array-based approaches as described below.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bp to about 1000 bases.

In some applications it is necessary to block the hybridization capacity of repetitive sequences. Thus, in some embodiments, tRNA, human genomic DNA, or Cot-1 DNA is used to block non- specific hybridization.

In comparative genomic hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the marker gene copy copy number.

Hybridization protocols suitable for use with the methods of the invention are described, e.g., in Albertson (1984) *EMBO J*. 3: 1227–1234; Pinkel (1988) *Proc. Natl. Acad. Sci. USA* 85: 9138–9142; EPO Pub. No. 430,402; *Methods in Molecular Biology, Vol.* 33: *In Situ Hybridization Protocols*, Choo, ed., Humana Press, Totowa, N.J. (1994), etc. In one particularly preferred embodiment, the hybridization protocol of Pinkel et al. (1998) *Nature Genetics* 20: 207–211, or of Kallioniemi (1992) *Proc. Natl Acad Sci USA* 89:5321–5325 (1992) is used.

2. Amplification-based assays.

In still another embodiment, amplification-based assays can be used to measure copy number. In such amplification-based assays, the marker nucleic acid sequences act as a template in an amplification reaction (e.g., Polymerase Chain Reaction (PCR). In a quantitative amplification, the amount of amplification product will be proportional to the amount of template in the original sample. Comparison to appropriate (e.g., healthy tissue) controls provides a measure of the copy number of the marker gene.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). The known nucleic acid sequence for the markers (see, for MKGenBank Accession Numbers U60669 S78775 and X59506) is sufficient to enable one of skill to routinely select primers to amplify any portion of the gene.

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

B. Detection of Gene Expression

As indicated above, the level of any of the present markers can also be assayed as a marker for a predilection to breast cancer.

In preferred embodiments, marker activity is characterized by a measure of marker gene transcript (e.g., MRNA), by a measure of the quantity of translated protein, or by a measure of enzymatic activity (e.g., pyruvate kinase activity in the case of M2-PK, or transcription based assays in the case of hnRNPK).

1. Detection of Gene Transcript.

a) Direct Hybridization Based Assays.

Methods of detecting and/or quantifying the level of a marker gene transcript (marker MRNA or cDNA made therefrom) using nucleic acid hybridization techniques are known to those of skill in the art (see, Sambrook et al., (1989) Molecular Cloning: A Laboratory Manual, 2d Ed., vols 1–3, Cold Spring Harbor Press, New York.

For example, one method for evaluating the presence, absence, or quantity of marker cDNA involves a Southern transfer as described above. Briefly, the MRNA is isolated (e.g., using an acid guanidinium-phenol-chloroform extraction method, Sambrook et al. supra.) and reverse transcribed to produce cDNA. The cDNA is then optionally digested and run on a gels in buffer and transferred to membranes. Hybridization is then carried out using the nucleic acid probes specific for the target cDNA.

The probes can be full length or less than the full length of the nucleic acid sequence encoding the protein. Shorter probes are empirically tested for specificity. Preferably nucleic acid probes are 20 bases or longer in length. (See Sambrook et al. for methods of selecting nucleic acid probe sequences for use in nucleic acid hybridization.) Visualization of the hybridized portions allows the qualitative determination of the presence or absence of cDNA.

Similarly, a Northern transfer may be used for the detection of an mRNA directly. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the mRNA.

b) Amplification-based Assays.

In another preferred embodiment, a marker transcript (e.g., M2-PK mRNA) can be measured using amplification (e.g PCR) based methods as described above for directly assessing copy number of the gene. In a preferred embodiment, a transcript level is assessed by using reverse transcription PCR (RT-PCR). As indicated above, PCR assay methods are well known to those of skill in the art. Similarly, RT-PCR methods are also well known.

C. Detection of Expressed Protein

The "activity" of a marker can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a typical embodiment, a marker polypeptide is detected using an immunoassay, such as an ELISA assay. As used herein, an immunoassay is an assay that utilizes an antibody to specifically bind to the analyte (i.e., the polypeptide). The immunoassay is thus characterized by detection of specific binding of a marker polypeptide to an anti-marker antibody as opposed to the use of other physical or chemical properties to isolate, target, and quantify the analyte.

The polypeptide is detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology Volume 37: Antibodies in Cell Biology*, Academic Press, Inc. New York; Stites & Terr (1991) *Basic and Clinical Immunology 7th Edition*.

Immunological binding assays (or immunoassays) typically utilize a "capture agent" to specifically bind to and often immobilize the analyte (in this case marker polypeptide or subsequence). The capture agent is a moiety that specifically binds to the analyte. In a preferred embodiment, the capture agent is an antibody that specifically binds a marker polypeptide. The antibody (anti-marker) may be produced by any of a number of means well known to those of skill in the art.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled marker polypeptide or a labeled anti-marker antibody. Alternatively, the labeling agent may be a third moiety, such as another antibody, that specifically binds to the antibody/marker polypeptide complex.

In one preferred embodiment, the labeling agent is a second human marker antibody bearing a label. Alternatively, the second marker antibody may lack a label, but it may, in turn, be bound by a labeled third antibody specific to antibodies of the species from which the second antibody is derived. The second can be modified with a detectable moiety, e.g., as biotin, to which a third labeled molecule can specifically bind, such as enzyme-labeled streptavidin.

Other proteins capable of specifically binding immuno-globulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom (1985) *J. Immunol.*, 135: 2589–2542).

As indicated above, immunoassays for the detection and/or quantification of marker polypeptide can take a wide variety of formats well known to those of skill in the art.

Preferred immunoassays for detecting a marker polypeptide are either competitive or noncompetitive. Noncompetitive immunoassays are assays in which the amount of captured analyte is directly measured. In one preferred "sandwich" assay, for example, the capture agent (anti-marker antibodies) can be bound directly to a solid substrate where they are immobilized. These immobilized antibodies then capture the marker polypeptide present in the test sample. The marker thus immobilized is then bound by a labeling agent, such as a second human marker antibody bearing a label.

In competitive assays, the amount of analyte (marker polypeptide) present in the sample is measured indirectly by measuring the amount of an added (exogenous) analyte (marker polypeptide) displaced (or competed away) from a capture agent (anti marker antibody) by the analyte present in the sample. In one competitive assay, a known amount of, in this case, marker polypeptide is added to the sample and the sample is then contacted with a capture agent. The amount of marker polypeptide bound to the antibody is inversely proportional to the concentration of marker polypeptide present in the sample.

In one particularly preferred embodiment, the antibody is immobilized on a solid substrate. The amount of marker polypeptide bound to the antibody may be determined either by measuring the amount of marker polypeptide present in an marker polypeptide /antibody complex, or alternatively by measuring the amount of remaining uncomplexed marker polypeptide. The amount of marker polypeptide may be detected by providing a labeled marker polypeptide.

The assays of this invention are scored (as positive or negative or quantity of marker polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of marker.

Antibodies for use in the various immunoassays described herein, can be produced according to standard methods (see, e.g., Harlow and Lane (1988) Antibodies: A Laboratory Manual, Cold Spring Harbor Press, NY.

Kits for providing the subject immunoassays are also provided. Generally, such kits comprise at least antibody specific for M2PK, hiRNPK, or any other protein described herein as well as any reagents necessary for the detection of antibody-marker binding complexes. The kits may further comprise other components of the immunoassay, such as solid support, solutions and the like.

It is particularly convenient in a clinical setting to perform the immunoassay in a self-contained apparatus, and such devices are provided by the subject invention. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the first antibody, and second labeled antibody combined with the assayed sample and the sandwich assay, e.g., ELISA assay, performed as above.

Such methods can also be used to distinguish between various forms of proteins. For example, M2PK can exist in a tetrameric and a dimeric form, which can be distinguished in a variety of ways, e.g., separation based on size. In such methods, cells can be extracted in a lysis buffer containing, e.g., 100 mM $N_2HPO_4$/$NaH_2PO_4$, 1 mM DTT, 1 mM NaF, 1 mM mercaptoethanole, 1 mM ε-aminocaproic acid, 0.2 mM PMSF, and 10% glycerol, pH 7.4.

1. Detection of Enzyme Activity.

In another embodiment, marker level (activity) is assayed by measuring the enzymatic activity of the marker polypeptide. Methods of assaying the activity of this enzyme are well known to those of skill in the art. For example, methods of measuring pyruvate kinase activity are well known and described, e.g., in Eigenbrodt et al. (1997), Brinck et al. (1994) Virchows Archiv 424:177–185, and Zweschke et al. (1999) *PNAS* 96:1291. Typically, M2-PK activity can be measured using high (2 mM) and low (0.2 mM) phosphoenolpyruvate concentrations. Also, glycolytic and glytaminolytic flux measurements can be made (see, e.g., Mazurek et al., (1997).

In addition, methods of detecting hnRNPK activity are well known. For example, hnRNPK cis-activates genes containing a CT promoter element such as CMYC. Thus, e.g., transcription based assays including CT promoters operably linked to reporter genes, e.g., luciferase or GFP, or DNA binding assays using CT promoter elements, can be used. Also, hnRNPK binds to a number of proteins, such as TBP, VAV oncoprotein, and the protein-tyrosine kinases SRC, FYN, and LYN (see, e.g. Ostareck-Lederer et al. (1998)). Protein binding assays using any of these proteins can be performed using standard techniques.

IV. Secondary Screening Steps

In numerous embodiments of the present invention, a secondary screening step will be performed. For example, if a level of one or more of the markers described herein is found to be elevated compared to a control level, then an additional method of detecting breast cancer will be performed to confirm the presence of the breast cancer. Any of a variety of secondary steps can be used, such as mammography, ultrasound, PET scanning, MRI, or any other imaging techniques, biopsy, clinical breast examination, ductogram, nipple discharge examination, or any other method.

V. Breast Cancers

The methods described herein can be used to detect any type of breast cancer. For example, adenocarcinoma, ductal carcinoma in situ (DCIS), infiltrating (or invasive) ductal carcinoma (IDC), infiltrating (or invasive) lobular carcinoma (ILC), inflammatory breast cancer, in situ, lobular carcinoma in situ (LCIS), medullary carcinoma, mucinous carcinoma, Paget's disease of the nipple, Phyllodes tumor, and tubular carcinoma can be detected. In addition, a breast cancer at any stage of progression can be detected, such as primary, metastatic, and recurrent breast cancer. Information regarding numerous types of breast cancer can be found, e.g., from the American Cancer Society (www3.cancer.org), or from, e.g., Wilson et al. (1991) Harrison's Principles of Internal Medicine, 12$^{th}$ Edition, McGraw-Hill, Inc.

VI. EXAMPLES

Example 1

Identifying ZNF217 as Amplified in Breast Cancer Cells

Gene amplification is frequently observed in malignant genomes and is believed to confer a selective growth advantage on the tumor cell. Whole genome scanning using comparative genomic hybridization has revealed ~20 regions of recurrent amplification in breast tumors. Genes expressed aberrantly due to amplification are involved in cell cycle regulation, metabolism, apoptosis, angiogenesis, transmembrane signaling, and resistance to chemotherapeutic agents. Amplification of 20q13.2 is particularly interesting because it is associated with aggressive tumor behavior, cellular immortalization, and occurs in a wide range of epithelial tumor types. Increased 20q13.2 copy-number is observed in ~18% of primary breast tumors whereas high level amplification occurs in ~10% of primary tumors (Tanner et al., 1994). High level amplification has been associated with decreased disease-free survival for breast cancer patients (Tanner et al., 1995; Courjal et al., 1996).

To identify the oncogene(s) driving amplification of 20q 13.2 a positional cloning and genomic sequencing strategy was pursued that has resulted in identification of seven genes ZNF217, ZNF218, NABC3, NABC2, NABC1, CYP24 and PIC-like. Of these genes only ZNF217 and NABC1 are expressed in breast cancer cell lines amplified at the 20q13.2 locus and only ZNF217 maps within the 260 kb minimum common amplicon defined in over 300 tumors and cell lines (Collins et al., 1998). ZNF217 is overexpressed in all tumors and cell lines in which it amplified and some in which it is not. The observation that ZNF217 is overexpressed in tumors in the absence of amplification indicates mechanisms independent of amplification can lead to aberrant expression. Sequence analysis indicates that ZNF217 belongs to the Kruppel-like family of transcription factors. Thus, ZNF217 emerged as a strong candidate for the oncogene driving 20q13.2 amplification (Collins et al., 1998).

Example 2

ZNF217 Immortalizes Cells in Culture

In an effort to elucidate ZNF217s role in breast carcinogenesis, we transfected ZNF217 into cultured human mammary epithelial cells (HMECs) using a retrovirus vector. HMECs transfected with ZNF217 became immortal. That is, ZNF217 transfectants were able to proliferate beyond 30 passages whereas HMECs infected with empty virus senesced at ~passage 15. Significantly, one of the immortal lines was assayed and found to have acquired telomerase activity.

Example 3

Identifying ZNF217-interacting Genes

A yeast two-hybrid screen was performed to identify proteins that interact with ZNF217. The ZNF217 transcriptional activation domains (+/−exon 4) were cloned into the pGBT9 vector. This vector is used to generate fusions with the target protein "bait" and GAL4 DNA-binding protein. The constructs were sequenced to confirm orientation, lack of mutations, and correct open reading frame. Transformation of yeast with the activation domain including exon 4 produced very low background indicating that the fusion proteins do not activate the HIS3 reporter gene on their own. A HeLa cell cDNA library constructed in the pGADGH vectors was then co-transformed into yeast strain HF7C with the activation domain containing exon 4 pGBT9 fusion.

Transformation of yeast with the activation domain containing exon 4 resulted in the isolation of 31 cDNAs. These cDNAs transactivated the HIS3 reporter gene in the presence of 2 mM 3-aminotriazole (AT), which increases the stringency of selection for His+. They did not transactivate in the absence of the ZNF217 bait DNA. Thus, activation depended on the presence of the ZNF217 construct. Sequencing revealed the cDNAs to be in-frame Gal4 fusions with one exception which was discarded. cDNAs were grouped into ten identity bins. Of these, seven are known genes, two are novel and one has proven difficult to sequence. Data base queries identified full-length sequence for seven cDNA clones and eight have chromosome assignments.

We have determined that the binding of both hnRNPK and M2PK are dependent upon the presence of ZNF217 exon 4. Exon 4 is alternatively processed and encodes 36 amino acids. In the case of M2PK we have tentatively identified the ZNF217-M2PK binding site through its homology with the OPA protein sequence that is believed to mediate OPA-M2PK binding (Williams et al., 1998). The peptide sequence is conserved in the murine ZNF217 protein and absent in the exon 4 minus isoform.

To assess the genomic copy-number and pattern of expression of the genes, we have isolated genomic DNA and total RNA from seven breast cancer cell lines, HMECs and HMECs immortalized by ZNF217. The breast cancer cell lines (BT474, MCF7, 600MPE, SKBR3, MDA436, HBL100, and MDA435) have between 2 and ~40 copies of the ZNF217 locus. A test genomic Southern blot containing only three cell lines (BT474, MCF7 and 600MPE) was hybridized with a cDNA identical to M2PK. This gene was found highly amplified (10–15-fold) in the MCF7 cell line. This demonstrates that in MCF7 M2PK is co-amplified with ZNF217 and it identifies a previously unrecognized amplicon at 15q22. M2PK and hnRNPK are highly expressed in breast cancer cell lines.

Multiple cDNAs homologous to transformation up-regulated protein or heterogeneous nuclear ribonuclear protein K (hnRNPK) were isolated in the yeast two-hybrid screen. In addition to M2PK and hnRNPK, we also recovered cDNAs identical to splicing factor Srp30c, cDNAs with homology to RNA binding proteins, and laminin binding protein. The heterogeneous ribonuclear protein complex is composed of ~20 proteins including hnRNPK and various splicing factors (Buchenau et al., 1997). Laminin binding protein has recently been shown to be associated with histones H2A, H2B and H4 (Kinoshita et al., 1998).

Example 4

Demonstration of Physical Interaction Between ZNF217 and Binding Partners

Physical interactions between ZNF217 and other molecules can be detected using the following methods. Direct binding is tested in vitro using GST pulldown experiments. ZNF217-binding proteins are cloned in-frame into a GST-fusion expression vector; proteins are expressed in bacteria and isolated/purified with glutathione affinity beads. The beads are then be incubated with in vitro translated and $^{35}$S-methionine labeled ZNF217. The resulting complex is isolated by centrifugation after extensive washing, and bound proteins separated by SDS-PAGE. Proteins are visualized by autoradiography or enhanced chemiluminescence detection.

To identify ZNF2 17 binding factors by immune precipitation, transfected and nontransfected cells are lysed in TNE buffer (10 mM Tris-HCl pH 7.4, 150 mM NaCl, 1 mM EDTA, 1 mM sodium orthovanadate [$Na_3VO_4$], 1 mM PMSF, 2 g of /ml leupeptin, and 2 g/ml aprotinin) with 1% NP-40 and clarified by centrifugation at 14,000×g for 10 min. Equal amounts of protein (500 g) are pre-cleared with Protein Asepharose (Zymed) and then incubated 2 hrs. at 4° C. with 5 g of the appropriate antibodies. Protein A-sepharose is added for 1 hr. at 4° C. and then washed 3 times with TNE buffer with 0.5 % NP-40. After immune precipitation, the bound proteins are separated by SDS-page and subjected to Western blotting using standard procedures. Co-immunoprecipitated complexes are probed with ZNF217 antibodies, antibodies directed against ZNF217-binding partners and specific co-activators and co-repressors.

REFERENCES

Alberts, A S; Frost, J A; Thorburn, A M. (1993) Rapid transcriptional assay for the expression of two distinct reporter genes by microinjection. DNA and Cell Biology. 12: 935–43.

Alberts, A S; Ceneste, O; Treisman, R. (1998) Activation of SRF-regulated chromosomal templates by Rho-family GTPases requires a signal that also induces H4 hyperacetylation. Cell. 92: 475–87.

Arias, J; Alberts, A S; Brindle, P; Claret, F X; Smeal, T; Karin, M; Feramisco, J; Montminy, M. (1994) Activation of cAMP and mitogen responsive genes relies on a common nuclear factor. Nature. 370: 226–9.

Buchenau, P; Saumweber, H; Arndt-Jovin, D J. (1997) The dynamic nuclear redistribution of an hnRNP K-homologous protein during Drosophila embryo development and heat shock. Flexibility of transcription sites in vivo. Journal of Cell Biology. 137: 291–303.

Collins, C; Rommens, J M; Kowbel, D; Godfrey, T; Tanner, M; Hwang, S I; Polikoff, D; Nonet, G; Cochran, J; Myambo, K; Jay, K E; Froula, J; Cloutier, T; Kuo, W L; Yaswen, P; Dairkee, S; Giovanola, J; Hutchinson, G B; Isola, J; Kallioniemi, O P; Palazzolo, M; Martin, C; Ericsson, C; Pinkel, D; Gray, J W; et al. (1998) Positional cloning of ZNF217 and NABC1: genes amplified at 20q13.2 and overexpressed in breast carcinoma. Proceedings of the National Academy of Sciences of the United States of America. 95: 8703–8.

Courjal, F; Cuny, M; Rodriguez, C; Louason, G; Speiser, P; Katsaros, D; Tanner, M M; Zeillinger, R& Theillet, C. (1996) DNA amplifications at 20q13 and MDM2 define distinct subsets of evolved breast and ovarian tumours. British Journal of Cancer. 74: 1984–1989.

Dejgaard, K; Leffers, H; Rasmussen, H H; Madsen, P; Kruse, T A; Gesser, B; Nielsen, H; Celis, J E. (1994) Identification, molecular cloning, expression and chromosome mapping of a family of transformation upregulated hnRNP-K proteins derived by alternative splicing. Journal of Molecular Biology. 236: 33–48.

Eigenbrodt, E; Reinacher, M; Scheefers-Borchel, U; Scheefers, H; Friis, R. (1992) Double role for pyruvate kinase type M2 in the expansion of phosphometabolite pools found in tumor cells. Critical Reviews in Oncogenesis. 3: 91–115.

Eigenbrodt, E; Basenau, D; Holthusen, S; Mazurek, S; Fischer, G. (1997) Quantification of tumor type M2 pyruvate kinase (Tu M2-PK) in human carcinomas. Anticancer Research. 17: 3153–6.

Hacker, H J; Steinberg, P; Bannasch, P. (1998) Pyruvate kinase isoenzyme shift from L-type to M2-type is a late event in hepatocarcinogenesis induced in rats by a cholinedeficient/DL-ethionine-supplemented diet. Carcinogenesis. 19: 99–107.

Hsieh, T Y; Matsumoto, M; Chou, H C; Schneider, R; Hwang, S B; Lee, A S; Lai, M M. (1998) Hepatitis C virus core protein interacts with heterogeneous nuclear ribonucleoprotein K. Journal of Biological Chemistry. 273: 17651–9.

Jewers, R J; Hildebrandt, P; Ludlow, J W; Kell, B; McCance, D J. (1992) Regions of human papillomavirus type 16 E7 oncoprotein required for immortalization of human keratinocytes. Journal of Virology. 66: 1329–35.

Kim, N W; Piatyszek, M A; Prowse, K R; Harley, C B; West, M D; Ho, P L; Coviello, G M; Wright, W E; Weinrich, S L; Shay, J W. (1994) Specific association of human telomerase activity with immortal cells and cancer. Science. 266: 2011–5.

Kinoshita, K; Kaneda, Y; Sato, M; Saeki, Y; Wataya-Kaneda, M; Hoffinann, A. (1998) LBP-p40 binds DNA tightly through associations with histones H2A, H2B, and H4. Biochemical and Biophysical Research Communications. 253: 277–82.

Mazurek, S; Hugo, F; Failing, K; Eigenbrodt, E. (1996) Studies on associations of glycolytic and glutaminolytic enzymes in MCF-7 cells: role of P36. Journal of Cellular Physiology. 167: 238–50.

Mazurek, S; Michel, A; Eigenbrodt, E. (1997) Effect of extracellular AMP on cell proliferation and metabolism of breast cancer cell lines with high and low glycolytic rates. Journal of Biological Chemistry. 272: 4941–52.

Mazurek, S; Grimm, H; Wilker, S; Leib, S; Eigenbrodt, E. (1998) Metabolic characteristics of different malignant cancer cell lines. Anticancer Research. 18: 3275–82.

Michelotti, E F; Michelotti, G A; Aronsohn, AI; Levens, D. (1996) Heterogeneous nuclear ribonucleoprotein K is a transcription factor. Molecular and Cellular Biology. 16: 2350–60.

Ostareck-Lederer, A; Ostareck, D H; Hentze, M W. (1998) Cytoplasmic regulatory functions of the KH-domain proteins hnRNPs K and E1/E2.Trends in Biochemical Sciences. 23: 409–11.

Phelps, WC; Yee, C L; Münger, K; Howley, PM. (1988) The human papillomavirus type 16 E7 gene encodes transactivation and transformation functions similar to those of adenovirus E1A. Cell. 53: 539–47.

Reznikoff, C A; Belair, C; Savelieva, E; Zhai, Y; Pfeifer, K; Yeager, T; Thompson, K J; DeVries, S; Bindley, C; Newton, M A; et al. (1994) Long-term genome stability and minimal genotypic and phenotypic alterations in HPV 16 E7-, but not E6-, immortalized human uroepithelial cells. Genes and Development. 8: 2227–40.

Samuels, M L; Weber, M J; Bishop, J M; McMahon, M. (1993) Conditional transformation of cells and rapid activation of the mitogen-activated protein kinase cascade by an estradiol-dependent human raf-1 protein kinase. Molecular and Cellular Biology. 13: 6241–52.

Savelieva, E; Belair, C D; Newton, M A; DeVries, S; Gray, J W; Waldman, F; Reznikoff, C A. (1997) 20q gain associates with immortalization: 20q13.2 amplification correlates with genome instability in human papillomavirus 16 E7 transformed human uroepithelial cells. Oncogene. 14: 551–60.

Sheets, M D; Amersdorfer, P; Finnern, R; Sargent, P; Lindqvist, E; Schier, R; Hemingsen, G; Wong, C; Gerhart, J C; Marks, J D. (1998) Efficient construction of a large nonimmune phage antibody library: the production of high-affinity human single-chain antibodies to protein antigens. Proceedings of the National Academy of Sciences of the United States of America. 95: 6157–62.

Solinas-Toldo, S; Durst, M; Lichter, P. (1997) Specific chromosomal imbalances in human papillomavirus-transfected cells during progression toward immortality. Proceedings of the National Academy of Sciences of the United States of America. 94: 3854–9.

Stampfer, M R; Bartley, J C. (1985) Induction of transformation and continuous cell lines from normal human mammary epithelial cells after exposure to benzo[a]pyrene. Proceedings of the National Academy of Sciences of the United States of America. 82: 2394–8.

Tanner, M M; Tirkkonen, M; Kallioniemi, A; Collins, C; Stokke, T; Karhu, R; Kowbel, D; Shadravan, F; Hintz, M; Kuo, W L; et al. (1994) Increased copy number at 20q13 in breast cancer: defining the critical region and exclusion of candidate genes. Cancer Research. 54: 4257–60.

Tanner, M M; Tirkkonen, M; Kallioniemi, A; Holli, K; Collins, C; Kowbel, D; Gray, J W; Kalliomiemi, O P & Isola, J. (1995) Amplification of chromosomal region 20q13 in invasive breast cancer: prognostic implications. Clinical Cancer Research. 1: 1455–1461.

Van Seuningen, I; Ostrowski, J; Bustelo, X R; Sleath, PR; Bomsztyk, K. (1995) The K protein domain that recruits the interleukin 1-responsive K protein kinase lies adjacent to a cluster of c-Src and Vav SH3-binding sites. Implications that K protein acts as a docking platform. Journal of Biological Chemistry. 270: 26976–85.

Walen, K H; Stampfer, M R. (1989) Chromosome analyses of human mammary epithelial cells at stages of chemical-induced transformation progression to immortality. Cancer Genetics and Cytogenetics. 37: 249–61.

Williams, J M; Chen, G C; Zhu, L; Rest, R F. (1998) Using the yeast two-hybrid system to identify human epithelial cell proteins that bind gonococcal Opa proteins: intracellular gonococci bind pyruvate kinase via their Opa proteins and require host pyruvate for growth.Molecular Microbiology. 27: 171–86.

Zhu, J; Woods, D; McMahon, M; Bishop, J M. (1998) Senescence of human fibroblasts induced by oncogenic Raf. Genes and Development. 12: 2997–3007.

Zwerschke, W; Mazurek, S; Massimi, P; Banks, L; Eigenbrodt, E; Jansen-Durr, P. (1999) Modulation of type M2 pyruvate kinase activity by the human papillomavirus type 16 E7 oncoprotein. Proceedings of the National Academy of Sciences of the United States of America. 96: 1291–6.

Example 5

NABC-1 Transforms NIH3T3 cells

As noted above, amplification of 20q13.2 is associated with aggressive tumor behavior and occurs in a wide range of epithelial tumor types. One of the genes in this region, designated 1b11 in the above reference PCT publication and referred to as NABC-1 here, was studied.

NABC-1 expression (by Northern blot analysis) could not be detected in human mammary epithelial cells (HMEC) or breast cancer cell lines not amplified at the 20q13 locus but is expressed at high level in 3 of 4 breast cancer cell lines with 20q13.2 amplification. Moreover, we have recently confirmed by immunocytochemistry that the NABC-1 gene product is overexpressed in some breast carcinoma lines but not detectable in HMEC. In addition, NABC-1 MRNA is expressed at high level in one of four primary tumors analyzed and, of perhaps significant importance, this tumor is not amplified at the NABC-1 locus.

The fact that NABC-1 is present in a region of the genome that is a recurrent region of amplification in breast cancer, and that the NABC-1 transcript and gene product are amplified in a majority of breast cancer cell lines that display amplification at 20q13.2, strongly indicates that this protein contributes to tumor formation. In addition, we have recently demonstrated that NIH-3T3 cells engineered to ectopically overexpress the NABC-1 gene product display a transformed phenotype.

As an initial step towards characterization of the NABC-1 gene product we have developed an antisera to this protein (designated pAb 760).

To investigate the functional consequences of $p60^{NABC-1}$ overexpression, we have introduced the NABC-1 cDNA into the murine cell line NIH-3T3 using retroviral transduction. Indirect immunofluorescence microscopy showed that 3T3 cells expressing this protein display specific perinuclear staining with pAb 760. This staining appears to indicate co-localization with the Golgi apparatus.

We have conducted a number of tests on these engineered NIH-3T3 cells. In particular we have examined cell growth characteristics and anchorage-dependent growth, two key hallmark features of cellular transformation. We have found that 3T3 expressing high levels of $p60^{NABC-1}$ show the propensity to form foci in culture as compared to control cell lines. We also discovered that a significant percentage of 3T3 cells expressing $p60^{NABC-1}$ form large colonies when grown in soft agar as compared to controls. Taken together, these observations indicate that $p60^{NABC-1}$ leads to transformation of NIH-3T3 cells.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of detecting a breast cancer in a patient suspected of having breast cancer, said method comprising:
   (i) providing a biological sample from said patient;
   (ii) detecting the level of M2 pyruvate kinase (M2 PK) within said biological sample; and
   (iii) comparing said level of M2 PK with a level of M2 PK in a control sample taken from a normal, cancer-free patient
   wherein an increased level of M2 PK in said biological sample compared to the level of M2 PK in said control sample indicates the presence of said breast cancer in said patient.

2. The method of claim 1, further comprising a secondary step, wherein an additional diagnostic step specific to breast cancer detection is performed on said patient.

3. The method of claim 2, said additional diagnostic step comprising mammography.

4. The method of claim 1, wherein said level of M2PK is detected by determining the copy number of M2PK genes in the cells of said biological sample.

5. The method of claim 1, wherein said level of M2PK is detected by measuring the level of M2PK protein in said biological sample.

6. The method of claim 5, wherein said biological sample is selected from the group consisting of excised tissue, whole blood, serum, plasma, saliva, cerebrospinal fluid, and urine.

7. The method of claim 6, wherein the biological sample is serum.

* * * * *